(12) United States Patent
Johnson

(10) Patent No.: US 7,582,343 B1
(45) Date of Patent: Sep. 1, 2009

(54) ELASTOMERIC ARTICLE WITH FINE COLLOIDAL SILICA SURFACE TREATMENT, AND ITS PREPARATION

(75) Inventor: David W. Johnson, Escondido, CA (US)

(73) Assignee: Kimberly-Clark Worldwide, Inc.

( * ) Notice: Subject to any disclaimer, the term of this patent is extended or adjusted under 35 U.S.C. 154(b) by 0 days.

(21) Appl. No.: 09/334,054

(22) Filed: Jun. 15, 1999

(51) Int. Cl.
B28B 23/00 (2006.01)

(52) U.S. Cl. ............... 428/36.4; 428/35.7; 428/145; 428/149; 2/167; 2/168; 2/161.7

(58) Field of Classification Search ............... 428/35.7, 428/143, 145, 149, 36.4; 2/161.8, 167, 168, 2/161.7; 427/203, 204
See application file for complete search history.

(56) References Cited

U.S. PATENT DOCUMENTS

| | | | |
|---|---|---|---|
| 3,637,416 A * | 1/1972 | Misch et al. | 428/412 |
| 3,787,229 A * | 1/1974 | Rudness | 117/132 BE |
| 4,027,060 A | 5/1977 | Esemplare et al. | |
| 4,070,713 A | 1/1978 | Stockum | 2/168 |
| 4,075,152 A | 2/1978 | Taller | |
| 4,082,862 A | 4/1978 | Esemplare et al. | |
| 4,100,309 A | 7/1978 | Micklus et al. | |
| 4,143,109 A | 3/1979 | Stockum | 264/112 |
| 4,204,907 A * | 5/1980 | Korklan et al. | 162/135 |
| 4,248,751 A | 2/1981 | Willing | 260/29.2 |
| 4,304,008 A | 12/1981 | Joung | 2/167 |
| 4,310,928 A | 1/1982 | Joung | |
| 4,329,312 A | 5/1982 | Ganz | 264/306 |
| 4,499,154 A | 2/1985 | James et al. | |
| 4,540,407 A | 9/1985 | Dunn | |
| 4,575,476 A | 3/1986 | Podell et al. | |
| 4,589,873 A | 5/1986 | Schwartz et al. | |
| 4,749,616 A | 6/1988 | Liu et al. | 428/331 |
| 4,851,266 A | 7/1989 | Momose et al. | 427/353 |
| 4,920,172 A | 4/1990 | Daoud | |
| 4,947,487 A | 8/1990 | Saffer et al. | |
| 5,008,178 A | 4/1991 | Van Thillo et al. | |
| 5,014,361 A | 5/1991 | Gray | |
| 5,069,965 A | 12/1991 | Esemplare | |
| 5,088,125 A | 2/1992 | Ansell et al. | |
| 5,138,719 A | 8/1992 | Orlianges et al. | 2/168 |
| 5,196,263 A | 3/1993 | Melby et al. | 428/327 |
| 5,213,887 A | 5/1993 | Huffman | |

(Continued)

FOREIGN PATENT DOCUMENTS

CS 9005117 A2 * 10/1990

(Continued)

*Primary Examiner*—Michael C Miggins
(74) *Attorney, Agent, or Firm*—Dority & Manning, P.A.

(57) ABSTRACT

A surface-modified article is formed of an elastomeric matrix, such as a glove shape, and a plurality of fine silica particles affixed to at least a portion of the surface of the matrix, the outside surface in the case of the glove. The fine silica particles increase the coefficient of friction of the article surface. The fine silica particles may also be made electrically conductive, so that static charge at the surface of the article is dissipated. The silica particles are applied by mixing them into a coating composition, applying the coating composition to the surface of a mold, and solidifying a flowable elastomeric composition against the coated surface. The coating composition may include a coagulant or a parting agent.

18 Claims, 3 Drawing Sheets

U.S. PATENT DOCUMENTS

| | | | |
|---|---|---|---|
| 5,244,728 A | 9/1993 | Bowman et al. | 428/330 |
| 5,272,012 A | 12/1993 | Opolski | |
| 5,272,771 A | 12/1993 | Ansell et al. | 2/167 |
| 5,284,607 A | 2/1994 | Chen | 264/37 |
| 5,310,517 A | 5/1994 | Dams et al. | |
| 5,332,612 A | 7/1994 | Payet et al. | 428/148 |
| 5,395,666 A | 3/1995 | Brindle | |
| 5,405,666 A | 4/1995 | Brindle | 428/36.4 |
| 5,438,709 A * | 8/1995 | Green et al. | 2/167 |
| 5,458,588 A | 10/1995 | Amdur et al. | 604/349 |
| 5,494,738 A | 2/1996 | Van Thillo et al. | |
| 5,534,350 A | 7/1996 | Liou | 428/423.1 |
| 5,536,569 A * | 7/1996 | Lasch et al. | 428/328 |
| 5,570,475 A | 11/1996 | Nile et al. | 2/161.7 |
| 5,571,219 A | 11/1996 | Gorton | |
| 5,587,351 A | 12/1996 | Morrison et al. | |
| 5,620,773 A * | 4/1997 | Nash | 428/145 |
| 5,691,069 A | 11/1997 | Lee | 428/500 |
| 5,700,585 A | 12/1997 | Lee | |
| 5,712,346 A | 1/1998 | Lee | |
| 5,728,340 A | 3/1998 | Dreibelbis et al. | |
| 5,742,943 A | 4/1998 | Chen | |
| 5,800,872 A | 9/1998 | Katz et al. | |
| 5,881,386 A | 3/1999 | Horwege et al. | |
| 5,932,299 A * | 8/1999 | Katoot | 427/508 |
| 5,977,223 A | 11/1999 | Ryan et al. | |
| 5,985,955 A | 11/1999 | Bechara et al. | |
| 5,993,923 A | 11/1999 | Lee | |
| 5,993,972 A | 11/1999 | Reich et al. | |
| 5,998,540 A | 12/1999 | Lipkin et al. | |
| 6,012,169 A | 1/2000 | Nishi et al. | |
| 6,017,997 A | 1/2000 | Snow et al. | |
| 6,051,320 A | 4/2000 | Noecker et al. | |

FOREIGN PATENT DOCUMENTS

| | | | |
|---|---|---|---|
| GB | 2321902 B | * | 5/1999 |
| JP | 59163404 | * | 5/1989 |
| JP | 02164527 A | * | 6/1990 |
| WO | WO9623643 | | 8/1996 |

* cited by examiner

ELASTOMERIC ARTICLE WITH FINE COLLOIDAL SILICA SURFACE TREATMENT, AND ITS PREPARATION

This invention relates to elastomeric articles such as gloves, and their surface treatment to improve properties.

Elastomeric materials are used in many types of articles because of their rubbery properties. They elastically elongate up to hundreds of percent, and then return to or toward their original shape when released. Protective gloves used in medical procedures and manufacturing operations are examples of the application of elastomers. Elastomers may be either natural or synthetic.

Elastomeric articles are typically tacky to the touch when initially manufactured. The tackiness increases the difficulty in handling the glove during manufacture, packaging the glove for sale and shipment, and donning the glove by the user. Elastomeric gloves are usually processed to reduce their tackiness. Historically, the most common processing to reduce tackiness has been the application of a powder such as cornstarch to the surface of the glove during manufacture. The use of a powder is acceptable for many glove applications. A powder may not be used for other applications, such as for surgical gloves, because the powder may find its way into the surgical wound. A powder may not be used for some manufacturing operations where gloves are required, because the powder may fall into sensitive structures being fabricated. Powder-free processing techniques have been developed for such applications.

Another of the problems experienced with elastomeric gloves is that their outer surfaces may become slippery when they are wet, so that the user of the glove may find it more difficult to grasp objects in the gloved hand without losing the grip. This slipperiness problem is particularly troublesome for gloves treated by powder-free processing techniques, because the very processing which reduces tackiness on the inside surface of the glove, thereby aiding donnability, also tends to modify the outside surface of the glove and reduce tackiness, thereby promoting loss of gripping power. Although efforts may be made to confine particular treatments to only the inside surface or the outside surface of the glove. these attempts have not been generally successful and have led to inconsistent results within lots of gloves.

The friction of the outside surface of the glove may instead be increased with a pattern of shallow ridges or the like on the outside surface. These features reduce the sensitivity of feel for the user of the glove, which is unacceptable for many applications such as medical and sensitive manufacturing operations.

There is a need for an approach to improving the friction of the outer surfaces of elastomeric gloves and the surfaces of other articles, which does not adversely affect other properties of the article and is consistent with powder-free manufacturing techniques. The present invention fulfills this need, and further provides related advantages.

SUMMARY OF THE INVENTION

This invention provides a surface-modified elastomeric article, such as a glove, and a method for its manufacture. The approach of the invention increases the surface friction of the outside surface of the glove. The approach is fully consistent with the use of powder-free manufacturing techniques and in those cases meets governmental requirements for powder-free articles. The improved outside-surface friction is achieved without modifying the basic physical structure of the article, without loss of the existing advantageous properties of the article, and with little increased cost. The treatment to achieve improved surface friction on some surfaces of the article may be applied in conjunction with other treatments of other surfaces of the article. For example, the outside surface of a glove may be treated to increase its friction, and the inside surface may be separately treated to improve its donnability without losing the increased friction on the outside surface. The mechanical properties of the basic glove are not sacrificed in order to attain improved donnability and grip retention. The surface modification of the article can also be made to increase the dissipation of static electrical charge, reducing the incidence of damage due to such static electrical charges. The processing approach leads to excellent consistency in batches of manufactured gloves.

In accordance with the invention, a surface-modified article comprises an elastomeric matrix having a surface, and a plurality of colloidal silica particles adhered to at least a portion of the surface of the matrix but not extending through the thickness of the matrix. The colloidal silica particles are affixed to the surface of the matrix, preferably without any separate binder material affixing the colloidal silica particles to the surface. In a preferred application, the elastomeric matrix is in the shape of a glove that receives the human hand therein. The matrix has an inside surface that contacts the human hand received within the hollow elastomeric glove shape, and an oppositely disposed outside surface. The colloidal silica particles are affixed to the outside surface of the glove.

The elastomer may be any operable material, such as natural latex, or a synthetic elastomer, such as styrene butadiene, neoprene, isoprene, nitrile, styrene-ethylene-butylene-styrene (S-EB-S), styrene-isoprene-styrene (S-I-S), or styrene-polybutydiene-styrene (S-B-S) rubbers. The colloidal silica particles desirably have a size of from about 10 nanometers to about 100 nanometers.

In one embodiment, the colloidal silica particles are themselves provided or treated so as to have some electrical conductivity. The electrical conductivity may be produced by depositing a partially conductive layer onto the surfaces of the particles, such as a thin surface layer of aluminum chlorhydrate. The electrical conductivity of the partially conductive colloidal silica particles improves the electrostatic discharge (ESD) properties of the article permitting static charge to dissipate more rapidly and completely than would otherwise be the case. Dissipation of static charge is an important requirement in many applications of elastomeric articles such as gloves, inasmuch as accumulated static charge in medical facilities or manufacturing plants may adversely affect treatments, instrumentation, and/or products.

The present invention also extends to a manufacturing method for preparing an article such as a glove. A method for making an elastomeric article comprises the steps of preparing a coating composition comprising a plurality of colloidal silica particles, providing a mold whose surface defines at least a portion of the surface of the elastomeric article, and applying the coating composition to a surface of the mold to achieve a coated surface. The method further includes contacting a flowable elastomer to the coated surface of the mold, allowing the flowable elastomer to coalesce against the coated surface, and separating the formed elastomer from the mold surface.

In the preferred embodiment, the mold is a glove shape former. The coating composition includes a coagulant having the colloidal silica particles mixed therewith. The mixture of coagulant and colloidal silica particles is applied to the surface of the glove former, which is dipped into the flowable elastomer and withdrawn, and the coagulated elastomer forms the matrix of the glove. The glove matrix is turned inside out, with the result that the outside surface has the plurality of colloidal silica particles thereon. Before it is turned inside out, the exposed surface of the glove matrix, which later becomes the inside surface of the glove, may be treated to improve handling characteristics and donnability with either powder-based or powder-free methods.

The present invention thus provides articles and a method for producing articles that have a surface selectively covered with colloidal silica particles. Chemical or coating-type powder-free de-tackifying treatments to the inside surface of the glove, even where they also are applied to the outside surface, do not adversely affect the gripping enhancement of the silica particles on the outside surface of the glove. The gripping enhancement is based on the physical structure at the outside surface, not on chemical effects. The present approach therefore allows powder or powder-free treatments to be applied to the glove, enhancing manufacturability, shipping, and donnability, while simultaneously achieving excellent grip retention even when the glove is wet.

The particles are selectively present on the surface of the article to provide increased friction. In presently preferred applications, no other material in the form of a binder is used to bind the colloidal silica particles to the surface of the article. On the other hand, carefully chosen surface coatings may be used to achieve particular results. Examples are polyether or polyester polyurethanes and certain extensible acrylate-based copolymers. To enhance ESD properties other additives such as metal oxides, alkali metal salts such as lithium nitrate and polyethylene ether glycols may be employed. The colloidal silica particles are present only on the treated surfaces, and do not extend through the body or thickness of the matrix. If the colloidal silica particles were mixed through the entire thickness of the article, there would be a potential for adverse effects on the mechanical properties of the article due to the high volume fraction of particles present. The present approach selectively positions the particles on the surface of the article where they are required to increase friction and/or for electrical charge dissipation.

Other features and advantages of the present invention will be apparent from the following more detailed description of the preferred embodiment, taken in conjunction with the accompanying drawings, which illustrate, by way of example, the principles of the invention. The scope of the invention is not, however, limited to this preferred embodiment.

DETAILED DESCRIPTION OF THE INVENTION

Figure 1:
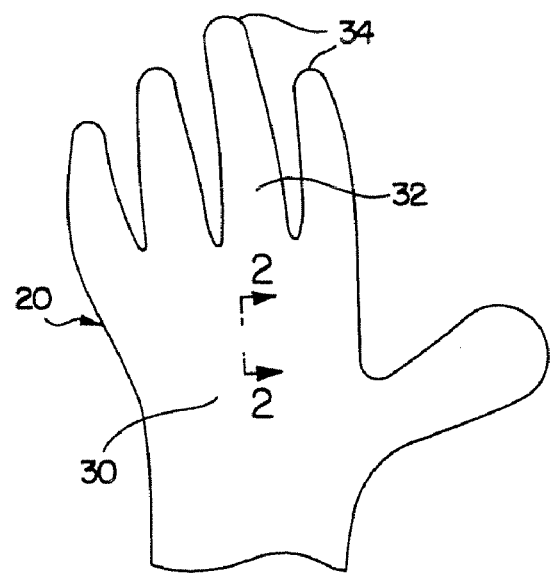
FIG. 1 is a perspective view of an article according to the invention, in this case a glove.

FIG. 1 illustrates an article according to the invention, in this case a preferred glove 20. The present invention is applicable to other articles as well, and is not limited to the glove 20.

Figure 2:
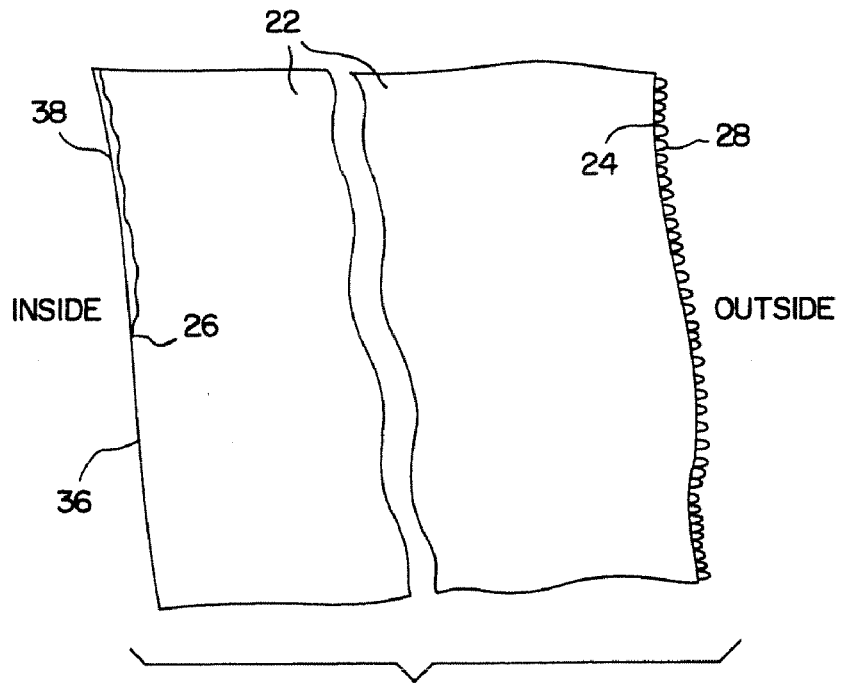
FIG. 2 is a schematic enlarged sectional view through the matrix in the region of the palm of the glove of FIG. 1, taken along lines 2-2.

FIG. 2 is a sectional view in the region of the palm of the glove 20, greatly enlarged to show the structures at the surfaces. The glove 20 is formed of an elastomer that is termed the "matrix" 22. The glove matrix 22 has an outside surface 24 and an inside surface 26. The inside surface 26 contacts the wearer's hand when the glove 20 is in use, and the outside surface 24 faces outwardly to contact gripped articles.

A plurality of particles 28 are adhered to at least a portion of the outside surface 24. The particles 28 are preferably colloidal silica ($SiO_2$) used in conjunction with the preferred manufacturing method to be described subsequently. Other types of particles, such as metal oxides (e.g., aluminum oxide) or combinations of colloidal silica and metal oxides may be used as well. Because colloidal silica particles are preferred, the remainder of the detailed description will be directed toward their use, with the understanding that other types of particles may be used.

Preferably, at least a palm 30 and gripping portions 32 of the fingers 34 of the outside surface 24 of the glove 20 have the colloidal silica particles 28 affixed thereto. Other portions of the glove 20, such as the portion overlying the back of the hand, need not have the colloidal silica particles adhered thereto, but no harm is done if the colloidal silica particles are present on these other portions as well. In a typical manufacturing operation, the colloidal silica particles will be adhered over the entire outside surface of the glove 20.

The inside surface 26 may be either exposed elastomer of the matrix 22, as in region 36, or it may be treated, as in region 38. Treatments to the inside surface 24 in the treated region 38 typically would be directed toward reducing the tackiness during manufacture and storage, and/or improving the donnability of the glove 20, because the inside surface 26 contacts the hand of the wearer when the glove 20 is used. A number of de-tackifying and donnability treatments are available, such as polymer coatings, powders, chlorination, and chemical treatments. Such donnability treatments are known in the art. A virtue of the use of colloidal silica particles 28 on the outside surface 24 is that it permits the use of no treatment on the inside surface 26, or any of a wide variety of treatments of the inside surface 26, without the loss of effectiveness of either the colloidal silica particles 28 on the outside surface 24 or the selected treatment on the inside surface 26. The colloidal silica particles 28 are a physical element, not a surface treatment that may be eradicated or negated by the treatment of the inside surface 26.

Figure 3:
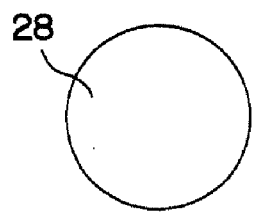
FIG. 3 is a schematic sectional view of a first embodiment of a silica particle.

FIG. 3 illustrates one of the particles 28 in greater detail. The preferred particles are generally spherical, with a maximum dimension (diameter) preferably from about 10 nanometers to about 100 nanometers, although other sizes may be operable. The particles having a size range of from about 10 nanometers to about 100 nanometers have been employed most effectively in manufacturing prototype gloves. The particles 28 reside on the treated outside surface 24, and may be partially embedded into the outside surface 24 so that a portion protrudes above the outside surface 24. The colloidal silica particles 28 at the outside surface 24 of the glove 20 increase the friction between the outside surface 24 and an article being grasped by the hand of the wearer of the glove 20. The particles 28 are not easily removed by subsequent processing such as donnability treatments applied to the inside surface, nor are they readily removed by ordinary use of the glove. Consequently, the array of colloidal silica particles 28 provides a durable friction-enhancing physical feature on the outside surface 24.

The colloidal silica particles 28 do not extend throughout the entire thickness of the matrix 22. They are not incorporated throughout the matrix by mixing them into the flowable elastomer from which the matrix is made. This distinction is an important one, because a high fraction of colloidal silica particles distributed throughout the matrix, when they are needed only at the outside surface 24, may result in adverse effects on the physical properties of the glove, particularly its limit of extensibility in tension without failure. The colloidal silica particles 28 are present substantially only on the outside surface 24, not throughout the matrix. Occasional colloidal silica particles 28 may be present in the matrix as a result of the manufacturing operation, but they are not intentionally distributed throughout the matrix.

Figure 4:
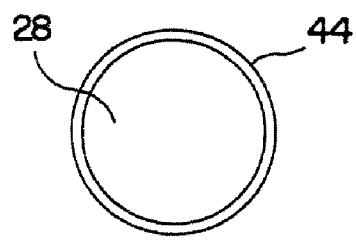
FIG. 4 is a schematic sectional view of a second embodiment of a silica particle.

FIG. 4 illustrates another type of colloidal silica particle 28. In this case, the particle 28 is made at least partially electrically conductive. In the pictured embodiment, the particles 28 have an electrically conductive surface treatment 44 applied thereto. An operable electrically conductive surface treatment 44 is the application of a thin layer of a metal or a metal-containing substance such as aluminum chlorhydrate. Equivalently for the present purposes, the particles 28 could be made partially electrically conductive throughout, as by doping the silica that forms the particles 28 with a metal such as aluminum.

The use of electrically conductive particles 28 allows localized high levels of electrical charge, such as static charge or tribocharge, to be dissipated through conduction along particle-to-particle contacts. This electrostatic discharge (ESD) may be important in certain glove applications. For example, medical gloves may experience local charging for any of several reasons, and the local charging may adversely affect instruments or treatments. Gloves used in clean room facilities may also experience local charging, which may be transferred to the articles being manufactured or interfere with manufacturing operations, in either case adversely affecting the quality of the final product. The present approach provides for a reduction of locally high concentrations of static charge, eventually bleeding the charge to low, harmless levels. This reduction of static charge is accomplished without embedding wires in the glove matrix or other techniques that have been previously proposed but which interfere with the utilization of the glove in service or with its mechanical properties such as its extensibility. In a typical case, electrostatic decay times are reduced from 8-20 seconds to as low as 0.3 seconds with the approach of the invention, measured by the static decay test approach of Federal Test Method Standard 101C Method 4046. Specifications are listed in EIA-541, Mil B-81705C, and NFPA 99.

Figure 5:
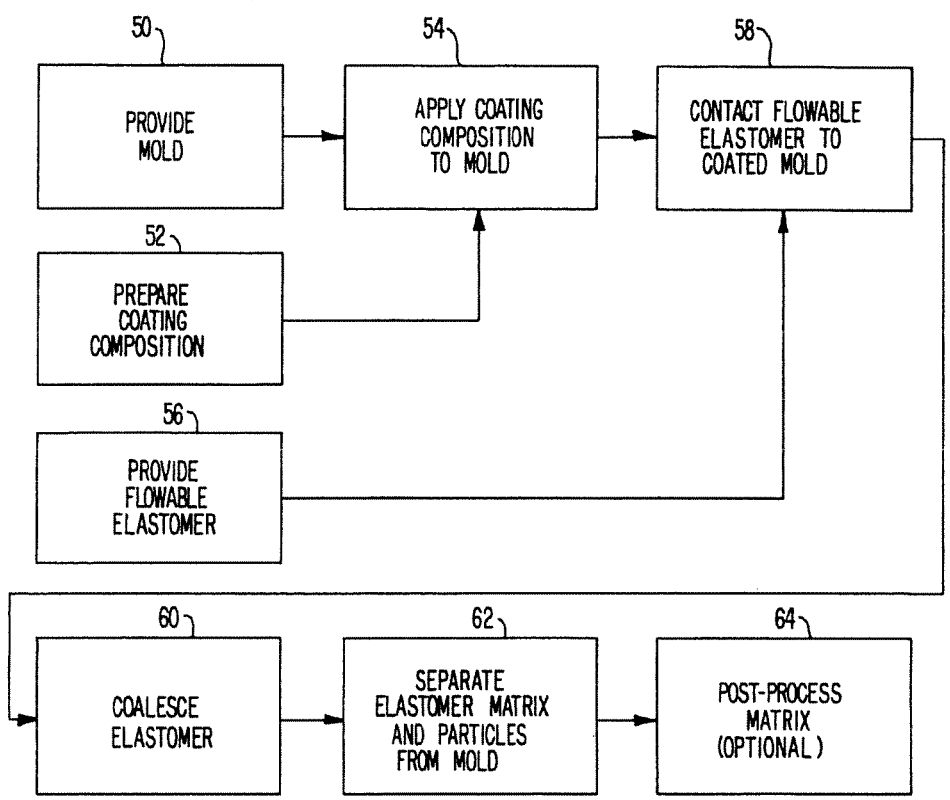
FIG. 5 is a block flow diagram of a method for practicing the invention.

FIG. 5 illustrates a preferred method for preparing an article, such as the glove 20, by the approach of the invention. A mold is provided, numeral 50. A surface of the mold defines at least a portion of the surface of the article to be manufactured, and in the preferred case defines the outside surface 24 of the glove 20. The mold for a glove is a shape of the human hand, known as a "former", made of glass, metal, porcelain, or other suitable material.

A coating composition is prepared, numeral 52. The coating composition includes the colloidal silica particles 28, mixed into a carrier which typically serves some other important function in the manufacture of the article. The colloidal silica particles are obtained commercially. Both untreated and electrically conductive colloidal silica particles are obtained from a vendor such as DuPont as Ludox® particles, or EKA Chemical as Bindzil® particles.

In the preferred case, the carrier is a coagulant for the elastomeric composition that forms the matrix of the glove. (The carrier could be selected as a mold release agent in other applications.) A suitable coagulant is an aqueous solution of about 10-30 percent by weight calcium nitrate or calcium chloride, about 0.1-0.5 percent by weight nonionic, cationic, or amphoteric surfactant, and about 0.001-0.2 percent by weight silicone or non-silicone dewebbing agent. This coagulant is acidic with a pH of about 3.5-6.0, which requires the use of the acid-compatible colloidal silica rather than other forms of particles that are not acid compatible.

The colloidal silica particles 28 are mixed into the carrier in a suitable loading, which is typically from about 0.1 to about 10 percent weight/weight for gloves. If a lesser amount of particles are used, they are largely ineffective. If a larger amount of particles are used, the surface of the elastomer becomes excessively tacky. The high tackiness is a disadvantage for gloves, but could be desirable for other products. Preferably, the loading of colloidal silica in the coagulant carrier is from about 0.5 to about 3.0 percent weight/weight. The resulting coating composition has a specific gravity of from about 1.18 to about 1.20, and a consistency like that of water.

The coating composition is applied to the mold surface and allowed to dry in place, numeral 54. Coating is accomplished by dipping the former into the coagulant mixture and drying it in an oven.

A flowable elastomer is provided, numeral 56. This flowable elastomer forms the matrix of the glove after processing. The flowable elastomer is an elastomeric material in an appropriate solvent that allows it to flow. Suitable elastomers include any operable material, such as natural latex elastomer, or a synthetic elastomer, such as styrene butadiene, neoprene, isoprene, nitrile, styrene-ethylene-butylene-styrene (S-EB-S), styrene-isoprene-styrene (S-I-S), or styrene-polybutydiene-styrene (S-B-S) rubbers. This listing of suitable elastomers is exemplary, not exhaustive. Solvents for the various elastomers are known in the art.

The flowable elastomer is contacted to the mold which has been previously coated with the coating composition, numeral 58. In the case of the manufacture of a glove, the former is dipped into the flowable elastomer. Dip forming technology is well known in the art, and will be described only briefly. The coagulant in the coating composition causes some of the flowable elastomer to become locally unstable and coagulate onto the surface of the former. During this process, the elastomer coalesces, numeral 60, capturing the particles 28 present in the coating composition at the surface of the coagulating elastomer. The former is withdrawn from the mass of flowable elastomer, and the coagulated layer is allowed to coalesce fully. A coating or donning agent may be applied to the glove either before or after curing. Each dip typically applies from about 0.05 to about 0.20 millimeter of elastomer to the surface of the former, and the presently preferred approach utilizes a single dip. If a thicker layer of elastomer is required, the former is re-dipped to apply more elastomeric material. The elastomer is gelled with heat to strengthen the elastomeric film, leached with flowing hot water to remove impurities, and cured with heat to vulcanize, in the case of rubber, nitrile, and neoprene, and dry the film.

The now-solid layer of elastomer, forming the matrix 22, is separated from the mold, numeral 62. In the case of a glove, the elastomer is turned inside-out when it is taken from the former, so that the portion of the glove initially contacting the former becomes its outside surface 24 with the colloidal silica particles 28 thereon. In the separation step 62, the colloidal silica particles serve as a functional replacement for powder as a release agent.

The article is optionally post-processed, numeral 64. The post processing may include further drying, chlorination, or other donnability treatments, for example. Such treatments are known in the art. The order of the separating step 62 and the post-processing step 64 may be reversed or the steps may be intermixed, so that some or all of the post-processing operations may be conducted with the glove still on the former, while some or all of the post-processing operations may be conducted with the glove removed from the former. As noted earlier, the post-processing operations have little effect on the silica particles affixed to the surface of the article.

The present invention has been successfully used to prepare gloves according to the preferred procedure discussed in relation to FIG. 5, using three matrix compositions: natural latex, and nitrile and styrene-butadiene synthetic rubbers.

A polymeric donnability-enhancing layer was applied to the inside surface of the natural latex gloves. These gloves were measured to determine their powder levels according to the procedures of ASTM D6124-97. Measured powder levels were about 0.2-0.3 milligrams of powder per glove, well below the maximum of 2 milligrams of powder per glove established by the Food and Drug Administration for powder-free articles. This result is significant, because substantially none of the silica particles were dislodged from the surface and measured as powder. Gloves made according to the present approach therefore qualify as powder-free gloves, if a powder-free donnability-enhancing treatment is applied to the inside surface of the glove. Protein levels in the absence of post processing were less than 50 parts per million. The coefficient of friction of the outside surface of the glove treated with the silica particles was increased by about 50-65 percent compared to gloves treated by other processes such as chlorination to render them powder free.

Although a particular embodiment of the invention has been described in detail for purposes of illustration, various modifications and enhancements may be made without departing from the spirit and scope of the invention. Accordingly, the invention is not to be limited except as by the appended claims.

What is claimed is:

1. A surface-modified glove comprising:
   an elastomeric matrix in the shape of a glove that receives a human hand therein, the matrix having an inside surface for contact with a human hand received within the glove and an outside surface; and
   a plurality of colloidal silica particles adhered to at least a portion of the outside surface of the matrix and partially embedded therein without extending through the thickness of the matrix, wherein there is no separate binder material affixing the colloidal silica particles to the outside surface.

2. The surface-modified glove of claim 1, wherein the elastomeric matrix comprises natural latex.

3. The surface-modified glove of claim 1, wherein the elastomeric matrix comprises a synthetic elastomer.

4. The surface-modified glove of claim 1, wherein the elastomeric matrix comprises a nitrile rubber.

5. The surface-modified glove of claim 1, wherein the colloidal silica particles have a maximum dimension of from about 10 nanometers to about 100 nanometers.

6. The surface-modified glove of claim 1, wherein the colloidal silica particles are electrically conductive.

7. The surface-modified glove of claim 1, wherein the colloidal silica particles further comprise an electrically conductive surface treatment thereon.

8. The surface-modified glove of claim 1, wherein the colloidal silica particles further comprise a layer of an electrically conductive material on the surface thereof.

9. The surface-modified glove of claim 1, wherein the colloidal silica particles further comprise a layer of aluminum chlorohydrate on the surface thereon.

10. The surface-modified glove of claim 1, further including an inside surface treatment on the inside surface.

11. A surface-modified glove, comprising:
    an elastomeric matrix having an outside surface; and
    a plurality of colloidal silica particles adhered to at least a portion of the outside surface of the matrix without any separate binder material, said particles being partially embedded in said outside surface without extending through the thickness of the matrix.

12. The surface-modified glove of claim 11, wherein the colloidal silica particles are electrically conductive.

13. A surface-modified glove, comprising:
    an elastomeric matrix having a surface; and
    a plurality of colloidal silica particles adhered to at least a portion of the surface of the matrix but not extending through the thickness of the matrix, the colloidal silica particles being affixed to the surface of the matrix without any separate binder material affixing the colloidal silica particles to the surface, wherein the colloidal silica particles are electrically conductive.

14. The surface-modified glove of claim 13, wherein the colloidal silica particles are partially embedded in the outside surface.

15. A surface-modified glove comprising:
    an elastomeric matrix in the shape of a glove adapted to receive a human hand therein, said elastomeric matrix having an inside surface for contact with a human hand received within the glove and an outside surface; and
    a surface treatment adhered to at least a portion of the outside surface of said glove, said surface treatment comprising a plurality of colloidal silica particles adhered to and partially embedded in said outside surface of said glove, wherein said silica particles are electrically conductive.

16. A glove as defined in claim 15, wherein said silica particles have a maximum dimension of from about 10 nanometers to about 100 nanometers.

17. A glove as defined in claim 15, wherein the silica particles further comprise a layer of aluminum chlorohydrate on the surface thereof.

18. A glove as defined in claim 15, wherein said silica particles are adhered to said outside surface of said glove by a binder.

* * * * *